United States Patent [19]

Alexander

[11] Patent Number: 4,705,897
[45] Date of Patent: Nov. 10, 1987

[54] PROCESS FOR PRODUCING BICYCLIC DIAMINES

[75] Inventor: David C. Alexander, Austin, Tex.

[73] Assignee: Texaco Inc., White Plains, N.Y.

[21] Appl. No.: 859,559

[22] Filed: May 5, 1986

[51] Int. Cl.⁴ .............................................. C07C 101/72
[52] U.S. Cl. ..................................... 564/445; 564/454
[58] Field of Search ................................ 564/454, 445

[56] References Cited

U.S. PATENT DOCUMENTS 3,492,330 1/1970 Trecker et al. .................. 564/454 X
3,894,995 7/1975 Reske et al. ...................... 564/454 X
4,118,499 10/1978 Stephenson et al. ........... 564/454 X Primary Examiner—Paul F. Shaver
Attorney, Agent, or Firm—Jack H. Park; Kenneth R. Priem; Cynthia L. Kendrick

[57] ABSTRACT

Bicyclic diamines are prepared by a process comprising reacting 5-vinyl-2-norbornene or norbornadiene, synthesis gas and an amine from the group consisting of primary amines and secondary amines in the presence of a catalyst comprising a ruthenium-containing compound, an amide solvent and a quaternary phosphonium salt.

15 Claims, No Drawings

PROCESS FOR PRODUCING BICYCLIC DIAMINES

FIELD OF THE INVENTION

This invention concerns a one step process for preparing disecondary or ditertiary diamines from inexpensive olefins, syngas and primary or secondary amines.

More particularly this invention relates to the catalytic aminomethylation of 5-vinyl-2-norbornene or norbornadiene to bicyclic diamines such as 2-(dimethylaminomethyl)-5-(3-dimethylaminopropyl)norbornane or 2-tertbutylaminomethyl 5-(3-tert-butylaminopropyl)norbornane by a process comprising adding carbon monoxide and hydrogen to said olefin substrate in the presence of an amine and a catalyst comprising a ruthenium-containing compound, an amide solvent and optionally a quaternary phosphonium salt. These compounds are useful as urethane catalysts.

BACKGROUND OF THE INVENTION

The concept of preparing bicyclic diamines from a bicyclic diolefin and a primary or secondary amine has apparently not been reported in the art.

Preparation of related compounds is described in German Offen. No. 2,163,753 to Hoechst (1973). In that patent diprimary amines are prepared from 2-vinyl-5-norbornene by a two step process comprising hydroformylation followed by reductive amination.

This two step process can be represented by the following equation:

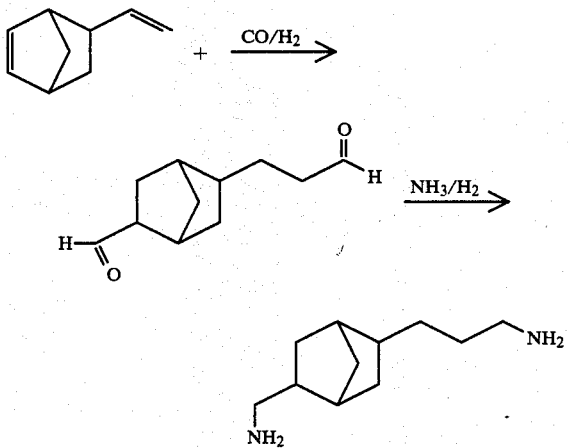

In U.S. Pat. No. 3,894,995 to Hoechst (1973), diprimary diamines such as those described above were found to be useful in the preparation of polyamide resins.

It would be a considerable advance in the art to produce bicyclic diamines from nonconjugated di-olefins, syngas and primary or secondary amines by a one step process. The product compounds may be used as rigid urethane foam catalysts and may possibly be used in RIM applications.

SUMMARY

This invention concerns a method for making bicyclic diamines as exemplified by 2-(dimethylaminomethyl)-5-(3-dimethylaminopropyl)norbornane and 2-(tert-butylaminomethyl)-5-3(tertbutylaminopropyl)norbornane which comprises contacting a mixture of olefin, synthesis gas and a primary or secondary amine with a catalyst system comprising a ruthenium-containing compound in an amide solvent, with, optionally, a quaternary phosphonium salt at a temperature of at least 100° C. and a pressure of at least 300 psi.

DETAILED DESCRIPTION

In the narrower and more preferred practice of this invention, bicyclic diamines are prepared from an olefin, synthesis gas (mixture of carbon monoxide and hydrogen) plus an amine by a process comprising:

(a) Contacting said mixture of olefin, carbon monoxide, hydrogen and amine with a catalyst system comprising a ruthenium-containing compound, an amide solvent, and, optionally, a quaternary phosphonium salt, (b) heating said reaction mixture to a temperature of at least 100° C. and a pressure of at least 300 psig and (c) separating said bicyclic diamines contained therein.

In order to present the inventive concept in the greatest possible detail to promote its understanding, the following supplementary disclosure is submitted. The basic invention improved upon here is practiced as follows:

Catalysts which are suitable in the practice of this invention contain ruthenium. The ruthenium-containing catalyst may be chosen from a wide variety of organic or inorganic compounds, complexes, etc. It is only necessary that the catalyst precursor actually employed contain said metal in any of its ionic states. The actual catalytically active species is then believed to comprise ruthenium in complex combination with carbon monoxide, hydrogen and a quaternary phosphonium salt in an amide solvent. The most effective catalyst is believed to be achieved where ruthenium oxides or ruthenium carbonyls are mixed in amide solvents optionally with quaternary phosphonium salts under reaction conditions.

The ruthenium catalyst precursors may take many different forms. For instance, the ruthenium may be added to the reaction mixture in an oxide form, as in the case of, for example, ruthenium(IV) oxide hydrate, anhydrous ruthenium(IV) dioxide and ruthenium(VIII) tetraoxide. Alternatively, it may be added as the salt of a mineral acid, as in the case of ruthenium(III) chloride hydrate, ruthenium(III) bromide, ruthenium(III) iodide, tricarbonyl ruthenium(II) iodide, anhydrous ruthenium(III) chloride and ruthenium nitrate, or as the salt of a suitable organic carboxylic acid, such as, for example, ruthenium(III) acetate, ruthenium naphthenate, ruthenium valerate and ruthenium complexes with carbonyl-containing ligands, such as ruthenium(III) acetylacetonate. The ruthenium may also be added to the reaction zone as a carbonyl or hydridocarbonyl derivative. Here, suitable examples include triruthenium dodecacarbonyl and other hydridocarbonyls such as $H_2Ru_4(CO)_{13}$ and $H_4Ru_4(CO)_{12}$, and substituted carbonyl species such as the tricarbonylruthenium(II) chloride dimer, $[Ru(CO)_3Cl_2]_2$.

Preferred ruthenium-containing compounds include oxides of ruthenium, ruthenium salts of an organic carboxylic acid and ruthenium carbonyl or hydridocarbonyl derivatives. Among these, particularly preferred are ruthenium (IV) dioxide hydrate, ruthenium tetraoxide, anhydrous ruthenium(IV) oxide, ruthenium acetate, ruthenium(III) acetylacetonate, and triruthenium dodecacarbonyl.

Especially good results were observed with triruthenium dodecacarbonyl and ruthenium oxide.

The quaternary onium salt which may optionally be used in the catalyst composition may be any onium salt but is preferably one of those containing phosphorus, such as those of the formula:

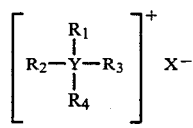

wherein Y is phosphorus, $R_1$, $R_2$, $R_3$ and $R_4$ are organic radicals, preferably alkyl, aryl or alkaryl radicals, and X is an anionic species. The organic radicals useful in this instance include those alkyl radicals having from 1 to 20 carbon atoms in a branched or linear alkyl chain, such as methyl, ethyl, n-butyl, isobutyl, octyl, 2-ethylhexyl and dodecyl radicals. Tetraethylphosphonium bromide and tetrabutylphosphonium bromide are typical examples presently in commercial production. The corresponding quaternary phosphonium acetates, nitrates, chromates, tetrafluoroborates and other halides, such as the corresponding chlorides, and iodides, are also satisfactory.

Equally useful are the phosphonium salts containing phosphorus bonded to a mixture of alkyl, aryl and alkaryl radicals, which radicals preferably contain from 6 to 20 carbon atoms. The aryl radical is most commonly phenyl. The alkaryl group may comprise phenyl substituted with one or more $C_1$ to $C_{10}$ alkyl substituents, bonded to phosphorus through the aryl function.

Illustrative examples of suitable quaternary onium salts include tetrabutylphosphonium bromide, heptyltriphenylphosphonium bromide, tetrabutylphosphonium iodide, tetrabutylphosphonium acetate, tetrabutylphosphonium nitrate, tetrabutylphosphonium chromate, tetraoctylphosphonium tetrafluoroborate, tetrahexylphosphonium acetate and methyl tri-n-butylphosphonium iodide.

The preferred quaternary onium salts and bases to be used in the process comprise the tetraalkylphosphonium salts containing alkyl groups having 1 to 6 carbon atoms, such as methyl, ethyl, butyl, hexyl, heptyl and isobutyl. Tetraalkylphosphonium salts, such as the halides, bromides, chlorides and iodides, and the acetate and chromate salts are preferred. Good results were observed with tetrabutylphosphonium bromide.

The olefinic substrates employed in the practice of this invention include unsaturated olefins containing from seven to twenty carbon atoms per molecule and having two olefinic groups therein. It is necessary that the olefin compounds contain two olefinic groups and further that the olefinic groups are nonconjugated. Nonconjugated olefins are the most suitable. Two olefins which work quite well are 5-vinyl-2-norbornene, the Diels-Alder product of butadiene and cyclopentadiene, and norbornadiene.

Based on earlier work with the ruthenium-catalyzed aminomethylation, the internal double bond might be expected to be relatively unreactive. Being part of the strained ring, however, this double bond is quite reactive toward many reagents.

Suitable nitrogen-containing coreactants useful in the practice of this invention include primary and secondary amines containing one to 20 carbon atoms. These amines may be straight or branched chain aliphatic series, they may be cycloaliphatic amines, or they may be aromatic amines. Examples of suitable primary aliphatic amines include methylamine, ethylamine, tert-butylamine, n-propylamine, n-hexylamine and n-dodecylamine. Secondary aliphatic amines that are satisfactory coreactants include dimethylamine, diethylamine, methylethylamine, di(n-propyl)amine, di(isopropyl)amine, di(ethylhexyl)amine, piperidine, morpholine, di(n-methyl)amine, and di(n-decyl)amine, as well as 2-aminooctane, N-methylaniline, and pyrrolidine. Aliphatic diamines such as piperazine are also useful in the practice of this invention. Ammonia is not effective in the process of this invention.

Amide solvents useful in the preparation of these diamines include N,N-dimethylformamide, N-methylpyrrolidone, N,N-dimethylacetamide, and N-hydroxyethylpyrrolidone. Use of these solvents leads to formation of a two-phase reaction mixture, and the catalyst can be removed from the product by separation of these layers.

The quantity of ruthenium compound, optional quaternary phosphonium salt and amide solvent employed in the instant invention is not critical and may vary over a wide range. In general, the novel process is desirably conducted in the presence of a catalytically effective quantity of active ruthenium species, optional quaternary phosphonium salt and an amide solvent which gives the desired product in reasonable yield. The reaction proceeds when employing as little as about $1 \times 10^{-6}$ weight percent and even lesser amounts of ruthenium.

The upper concentration is dictated by a variety of factors including catalyst cost, partial pressure of carbon monoxide and hydrogen, operating temperature, etc. A ruthenium concentration of from about 0.0001 to about 1 weight percent in conjunction with a quaternary phosphonium concentration of from about 0.001 to about 10 weight percent and a solvent concentration of from about 10 to about 70 based on the total weight of the reaction mixture is desirable in the practice of this invention.

The temperature range which can usefully be employed in these syntheses is a variable dependent upon other experimental factors, including the pressure, the concentration and the choice of the particular species of ruthenium catalyst among other things. The range of operability is from about 100° to 300° C. when superatmospheric pressures of syngas are employed. A narrow range of 130°–200° C. represents the preferred temperature range.

Superatmospheric pressures of 100 psi or greater lead to substantial yields of tertiary or secondary amines by the process of this invention. A preferred operating range is above 300 psi. The most preferred range is from 400–5000 psi, but pressures greater than 5000 psi can be used.

The relative amounts of carbon monoxide and hydrogen which may be initially present in the syngas mixture are variable, and these amounts may be varied over a wide range. In general, the mole ratio of CO-to-$H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases of the group including nitrogen, argon, neon and the like, or they may include gases that may or may not undergo reaction under CO hydrogenation conditions, as represented by carbon dioxide and hydrocarbons including methane, ethane, propane and the like, ethers such as dimethyl ether, methylethyl ether and diethyl ether, alkanols such as methanol and acid esters such as methyl acetate.

In all these syntheses, the amount of carbon monoxide and hydrogen present in the reaction mixture should be sufficient to at least satisfy the stoichiometry of the desired aminomethylation reaction.

The novel process of this invention can be conducted in a batch, semi-continuous or continuous fashion and said material may be recovered by methods well known in the art, such as distillation, fractionation, extraction and the like.

The major products of these syntheses are diamines, particularly bicyclic diamines such as 2-(dimethylaminomethyl)-5-(3-dimethylaminopropyl)norbornane and 2-(tert-butylaminomethyl)-(5-3-tert-butylaminopropyl)norbornane. The principal by-products of these preparations are dimethylamine, dimethylacetamide, and dimethylformamide.

The products have been identified in this work by one or more of the following analytical procedures, viz, gas-liquid phase chromatography (glc), infrared (ir), mass spectrometry, proton nuclear magnetic resonance (H'-nmr) and elemental analyses, or a combination of these techniques. All temperatures are in degrees centigrade and all pressures are in pounds per square inch gauge (psig).

Having described the inventive process, the following examples are submitted to supply specific and illustrative embodiments.

EXAMPLE I (5713-98)

Example I demonstrates a typical preparation of one of the compounds of this invention, 2-(dimethylaminomethyl)-5(or 6)-(3-dimethylaminopropyl)norbornane.

To a one liter stainless steel stirred autoclave was added 5-vinyl-2-norbornene (180 ml, 1.25 mol), N,N-dimethylacetamide (100 ml), ruthenium oxide hydrate (0.5 g, 3 mmol), and tetrabutylphosphonium bromide (4.5 g, 13.3 mmol). After the autoclave was sealed and flushed with 1/1 CO/H$_2$, dimethylamine (170 ml, 2.6 mol) was pressured in. The mixture was then pressured to 500 psi and heated to 150° C. The pressure fell to 450 psi at the end of the heating period and was increased to 1000 psi. Periodic repressurizations to 1000 psi were made during the course of the reaction and stirring at 150° C. was continued for 7 hours. The product consisted of a light orange upper layer (240 ml) and a darker orange lower layer (160 ml). The upper layer was found to contain less than 4% unreacted vinylnorbornene; the monoamine (1) and diamine (2) isomeric mixtures were present in a ratio of approximately 1/1 and together composed 75% of the reaction mixture. The remainder of the upper layer consisted of dimethylamine, dimethylacetamide, and dimethylformamide. The upper layer was distilled under a vacuum of 0.5 mm Hg and gave 75 g of the isomeric ditertiary diamines (identified by nmr), boiling at 110°–115° C. (5751-98).

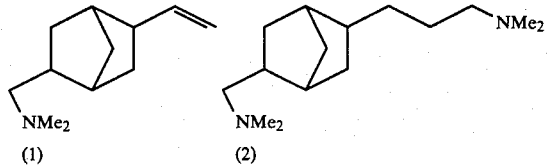

(1)         (2)

EXAMPLE II

Example II demonstrates the preparation of another compound of this invention,)2-tert-butylaminomethyl-5-(or 6)-(3-tert-butylaminopropyl)norbornane.

To a 300 ml stainless steel stirred autoclave were added 5-vinyl-2-norbornene (10 ml, 70 mmol), tert-butylamine (17 ml, 164 mmol), N,N-dimethylformamide (10 ml), triruthenium dodecacarbonyl (0.1 g, 0.156 mmol), and tetrabutylphosphonium bromide (1.0 g, 2.95 mmol). The autoclave was sealed and flushed with 1/1 CO/H$_2$, then pressurized to 500 psi with 1/1 CO/H$_2$. The mixture was then stirred for 3 hours at 150° C. with periodic repressuring to maintain 700–750 psi. As in the previous reaction, the product was found to consist of two layers, the upper was light orange (20 ml) and the lower dark orange (15 ml). The upper layer consisted primarily (75%) of a mixture of monoamine (3) (and isomers) and diamine (4) (and isomers) in a ratio of 4/1. The remainder of the upper layer consisted of dimethylamine and dimethylformamide. The upper layer was distilled under a vacuum of 0.14 mm Hg, and gave 6.8 g of isomeric diamines (identified by nmr) boiling at 128°–135° C. (5713-59).

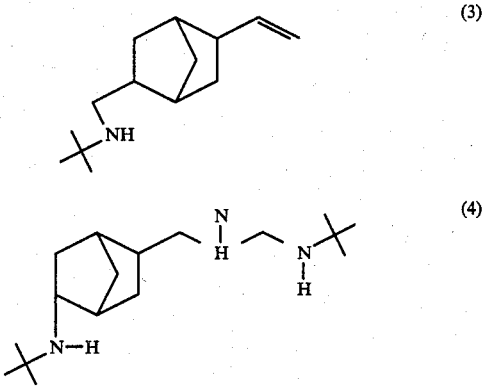

EXAMPLE III

The product from Example I was used to catalyze the preparation of a rigid polyurethane foam.

The foam was prepared from polymeric isocyanate PAPI-27 (a, 48.7 pbw) and a mixture consisting of THANOL ® R-480 (b, 36.3 pbw), L-5240 (c, 0.5 pbw), trichlorofluoromethane (14.0 pbw), and diamine 5713-98 (0.8 pbw). The following characteristics were observed in two foam preparations (5735-39):

| | | |
|---|---|---|
| cream time (sec) | 29 | 28 |
| gel time (sec) | 86 | 84 |
| tack free time (sec) | 104 | 98 |
| rise time (sec) | 140 | 140 |
| initial surface friability | good | good |

(a) Polymeric isocyanate sold by Upjohn.
(b) Sucrose-amine polyol sold by Texaco Chemical Co.
(c) Silicone surfactant sold by Union Carbide.

EXAMPLE IV

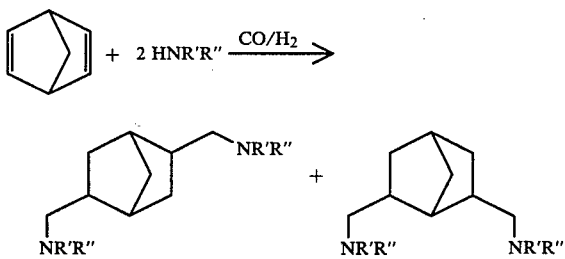

In Example IV the use of norbornadiene in the preparation of bicyclic diamines (2,5- and 2,6-bis(diethylaminomethyl)norbornane) is demonstrated. Norbornadiene (8.5 g, 90 mmol), diethylamine (13.5 g, 184 mmol), triruthenium dodecacarbonyl (0.15 g, 0.23 mmol), and N,N-dimethylformamide (10 ml) were charged to a 300 ml stainless steel stirred autoclave, which was sealed and flushed with ½ $CO/H_2$. The mixture was then pressurized to 500 psi and heated at 160° C. for four hours with periodic repressuring to 500–600 psi. The product was found to consist of an upper light orange layer (20 g) and a lower dark orange layer (10 g). In the upper layer was a small amounts of unreacted diethylamine and norbornadiene and a mixture of isomeric diamines and monoamines in a 60/40 ratio (identified by nmr).

What is claimed is:

1. A one step process for preparing bicyclic diamines which comprises reacting 5-vinyl-2-norbornene, synthesis gas and an amine from the group consisting of primary amines and secondary amines in the presence of a catalyst comprising a ruthenium-containing compound, an amide solvent and, optionally, a quaternary phosphonium salt.

2. The process of claim 1 wherein the amine used is a primary amine selected from the group consisting of methylamine, ethylamine, n-propylamine, n-hexylamine and n-dodecylamine, and tert-butylamine.

3. The process of claim 1 wherein the amine used is a secondary amine selected from the group consisting of dimethylamine, diethylamine, methylethylamine, di(n-propyl)amine, di(iso-propyl)amine, di(ethylhexyl)amine, dimethylamine, di(n-decyl)amine, 2-aminooctane, N-methylaniline, and pyrrolidine.

4. The process of claim 3 wherein the amine used is diethylamine.

5. The process of claim 1 wherein the ruthenium-containing compound is from the group consisting of oxides of ruthenium, ruthenium salts of a mineral acid, ruthenium salts of a carboxylic acid and ruthenium carbonyls.

6. The process of claim 1 wherein the ruthenium-containing compound is selected from the group consisting of ruthenium(IV) dioxide hydrate, ruthenium tetraoxide, anhydrous ruthenium (IV) oxide, ruthenium acetate, ruthenium acetylacetonate and triruthenium dodecacarbonyl.

7. The process of claim 4, wherein the ruthenium-containing compound is selected from the group consisting of triruthenium dodecacarbonyl and ruthenium oxide hydrate.

8. The process of claim 1 wherein the quaternary phosphonium salt is a tetraalkylphosphonium salt.

9. The process of claim 8 wherein the tetraalkylphosphonium salt is selected from the group consisting of tetrabutylphosphonium bromide, heptyltriphenylphosphonium bromide, tetrabutylphosphonium iodide, tetrabutylphosphonium acetate, tetrabutylphosphonium nitrate, tetrabutylphosphonium chromate, tetraoctylphosphonium tetrafluoroborate, tetrahexylphosphonium acetate and methyl tri-n-butylphosphonium iodide.

10. The process of claim 9 wherein the tetraalkylphosphonium salt is tetrabutylphosphonium bromide.

11. The process of claim 1 wherein the process takes place at a temperature between 100° C. and 300° C.

12. The process of claim 1 wherein the process takes place at a pressure between 400 psi and 5000 psi.

13. A one step process for simultaneously preparing 2-(dimethylaminomethyl)-5-(3-dimethylaminopropyl)-norbornane and 2-(tert-butylaminomethyl)-5-(3-tert-butylaminopropyl)norbornene which comprises reacting 5-vinyl-2-norbornene, synthesis gas and an amine from the group consisting of dimethylamine, tert-butylamine, diethylamine, N,N-dimethylacetamide and N,N-dimethylformamide at a temperature above 100° C. and a pressure above 400 psi.

14. A diamine of the formula:

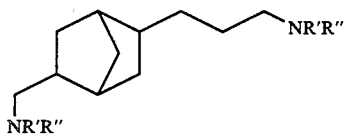

wherein R' comprises a $C_1-C_{20}$ alkyl or H
and R" comprises the same or different $C_1-C_{20}$ alkyl which is a useful component in catalysts for the formation of urethanes.

15. A diamine of the formula:

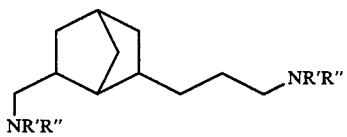

wherein R' comprises a $C_1-C_{20}$ alkyl or H
and R" comprises same or different $C_1-C_{20}$ alkyl which is a useful component in catalysts for the formation of urethanes.

* * * * *